United States Patent [19]

Lai

[11] Patent Number: 5,747,532
[45] Date of Patent: May 5, 1998

[54] COMBINATIONAL THERAPEUTIC METHODS EMPLOYING NITRIC OXIDE SCAVENGERS AND COMPOSITIONS USEFUL THEREFOR

[75] Inventor: Ching-San Lai, Encinitas, Calif.

[73] Assignee: Medinox, Inc., San Diego, Calif.

[21] Appl. No.: 561,594

[22] Filed: Nov. 21, 1995

[51] Int. Cl.$^6$ ............................................. A61K 31/325
[52] U.S. Cl. ................... 514/491; 424/93.7; 424/145.1; 424/158.1; 514/4; 514/45; 514/162; 514/171; 514/305; 514/313; 514/352
[58] Field of Search ............................................. 514/491

[56] References Cited

U.S. PATENT DOCUMENTS

| | | | |
|---|---|---|---|
| 4,160,452 | 7/1979 | Theeuwes | 424/427 |
| 4,256,108 | 3/1981 | Theeuwes | 424/424 |
| 4,265,874 | 5/1981 | Bonsen et al. | 424/473 |
| 5,358,703 | 10/1994 | Lai | 424/9.33 |

OTHER PUBLICATIONS

Hamid et al., "Induction of nitric oxide synthase in asthma", Lancet, 342, pp. 1510-1513, 1993.
Eizirik et al., "Cytokines Suppress Human Islet Function Irrespective of Their Effects on Nitric Oxide Generation", J. Clin. Invest., 93, pp. 1968-1974, 1994.
Chemical Abstracts 109:108420. Von Ritter et al. "Gastric mucosal lesions induced by hemorrhagic shock in baboons. Role of oxygen-derived free radicals.", Dig. Dis. Sci. 33(7), pp. 857-864, 1988.
Choi, P.M., "Immunomodulator Therapy in Inflammatory Bowel Disease", Digestive Diseases and Sciences, 39 (9), pp. 1885-1892, 1994.
Rachmilewitz, D., et al. "Enhanced colonic nitirc oxide generation and nitric oxide synthase activity in ulcerative colitis and Crohn's disease", Gut, 36(5), pp. 718-723, May 1995.
Aisaka et al., "N$^G$-Methylarginine, an Inhibitor of Endothelium-Derived Nitric Oxide Synthesis, is a Potent Pressor Agent in the Guinea Pig: Does Nitric Oxide Regulate Blood Pressure In Vivo?" Biochem. Biophys. Res. Commun. 160(2):881-886 (1989).
Aisaka et al., "L-Arginine Availability Determines the Duration of Acetylcholine-Induced Systemic Vasodilation In Vivo" Biochem. Biophys. Res. Commun. 163(2):710-717 (1989).
Akaike et al., "Therapeutic Effects of Imidazolineoxyl N-Oxide Against Endotoxin Shock Through Its Direct Nitric Oxide-Scavenging Activity" Biochem. Biophys. Res. Commun. 202(2):923-930 (1994).
Alving et al., "Increased Amount of Nitric Oxide in Exhaled Air of Asthmatics" Eur. Respir. J. 6:1368-1370 (1993).
Balter, Michael, "Cytokines Move From the Margins Into the Spotlight" Science 268:205-206 (1995).
Barnes and Liew, "Nitric Oxide and Asthmatic Inflammation" Immunology Today 16(3):128-130 (1995).

Boughton-Smith et al., "Nitric Oxide Synthase Activity in Ulcerative Colitis and Crohn's Disease" Lancet 342:338-340 (1993).
Bredt and Snyder, "Nitric Oxide: A Physiologic Messenger Molecule" Ann. Rev. Biochem. 63:175-95 (1994).
Bukrinsky et al., "Regulation of Nitric Oxide Synthase Activity in Human Immunodeficiency Virus Type 1 (HIV-1)-infected Monocytes: Implications for HIV-associated Neurological Disease" J. Exp. Med. 181:735-745 (1995).
Cattell et al., "Localization of Inducible Nitric Oxide Synthase in Acute Renal Allograft Rejection in the Rat" Transplantation 58(12):1399-1402 (1994).
Clària et al., "Pathogenesis of Arterial Hypotension in Cirrhotic Rats with Ascites: Role of Endogenous Nitric Oxide" Hepatology 15:343-349 (1992).
Corbett et al., "Nitric Oxide Mediates Cytokine-Induced Inhibition of Insulin Secretion by Human Islets of Langerhans" Proc. Natl. Acad. Sci. USA 90:1731-1735 (1993).
Devlin et al., "Nitric Oxide Generation" Transplantation 58:592-595 (1994).
Diket et al., "Nitric Oxide Inhibition Causes Intrauterine Growth Retardation and Hind-Limb Disruptions in Rats" Am. J. Obstet. Gynecol. 171:1243-1250 (1994).
Dorheim et al., "Nitric Oxide Synthase Acitivity is Elevated in Brain Microvessels in Alzheimer's Disease" Biochem. Biophys. Res. Commun. 205:659-665 (1994).
Eizirik et al., "Major Species Differences Between Humans and Rodents in the Susceptibility to Pancreatic β-Cell Injury" Proc. Natl. Acad. Sci. USA 91:9253-9256 (1994).

(List continued on next page.)

Primary Examiner—C. Warren Ivy
Assistant Examiner—Lyman H. Smith
Attorney, Agent, or Firm—Gray Cary Ware & Freidenrich; Stephen E. Reiter

[57] ABSTRACT

In accordance with the present invention, there are provided combinational therapeutic methods for the in vivo inactivation or inhibition of formation (either directly or indirectly) of species which induce the expression of nitric oxide synthase, as well as reducing nitric oxide levels produced as a result of .NO synthase expression. In contrast to the inhibitory approach described in the prior art (i.e., wherein the function of the enzymes responsible for nitric oxide production is inhibited), the present invention employs a combination of inactivation (or inhibition) and scavenging approach whereby the stimulus of nitric oxide synthase expression is inactivated, or the production thereof is inhibited, and overproduced nitric oxide is bound in vivo to a suitable nitric oxide scavenger. The resulting complexes render the stimulus of nitric oxide synthase expression inactive (or inhibit the production thereof), and nitric oxide harmless. The resulting complexes are eventually excreted in the urine of the host. Further in accordance with the present invention, there are provided compositions and formulations useful for carrying out the above-described methods.

33 Claims, 1 Drawing Sheet

OTHER PUBLICATIONS

Evans et al., "Inhibition of Nitroc Oxide Synthase in Experimental Gram-Negative Sepsis" *J. Infect. Dis.* 169:343–349 (1994).

Evans et al., "Evidence of Increased Nitric Oxide Production in Patients With the Sepsis Syndrome" *Circulatory Shock* 41:77–81 (1993).

Farrel et al., "Increased Concentrations of Nitrite in Synovial Fluid and Serum Samples Suggest Increased Nitric Oxide Synthesis in Rheumatic Diseases" *Annals of Rhumatic Diseases* 51:1219–1222 (1992).

Glauser et al., "Pathogenesis and Potential Strategies for Prevention and Treatment of Septic Shock: An Update" *Clin. Infect. Dis.* 18:S205–16 (1994).

Gómez-Jiménez et al., "L-Agrinine: Nitric Oxide Pathway in Endotoxemia and Human Septic Shock" *Critical Care Medicine* 23:253–258 (1995).

Guarner et al., "Increased Serum Nitrite and Nitrate Levels in Patients with Cirrhosis: Relationship to Endotoxemia" *Heptology* 18:1139–1143 (1993).

Hamid et al., "Induction of Nitric Oxide Synthase in Asthma" *Lancet* 342:1510–1513 (1993).

Harbrecht et al., "Inhibition of Nitric Oxide Sythesis During Endotoxemia Promotes Intrahepatic Thrombosis and an Oxygen Radical–Mediated Hepatic Injury" *J. Leuk. Biol.* 52:390–394 (1992).

Henderson et al., "The Effects of Nitric Oxide Ingibition on Regional Hemodynamics During Hyperdynamic Endotoxemia" *Arch. Surg.* 129:1271–1275 (1994).

Hibbs et al., "Evidence for Cytokine-Inducible Nitric Oxide Synthesis from L-Arginine in Patients Receiving Interleukin-2 Therapy" *J. Clin. Invest.* 89:867–877 (1992).

Hotchkiss et al., "Inhibition of NO Synthesis in Septic Shock" *Lancet* 339:434–435 (1992).

Ignarro et al., "Endothelium-Derived Relaxing Factor Produced and Released From Artery and Vein is Nitric Oxide" *Proc. Natl. Acad. Sci., USA* 84:9265–69 (1987).

Ignarro, L.J., "Biosynthesis and Metabolism of Endothelium-Derived Nitric Oxide" *Ann. Rev. Toxicol.* 30:535–560 (1990).

Johnson et al., "Evidence for Increased Nitric Oxide Production in Multiple Sclerosis" *Journal of Neurology, Neurosurgery and Phyciatry* 58:107 (1995).

Kaur and Halliwell, "Evidence for Nitric Oxide Mediated Oxidative Damage in Chronic Inflammation" *FEBS Letters* 350:9–12 (1994).

Kharitonov et al., "Increased Nitric Oxide in Exhaled Air of Asthmatic Patients" *Lancet* 343:133–135 (1994).

Kilbourn et al., "$N^G$-Methyl-L-Arginine Inhibits Tumor Necrosis Factor-Induced Hypotension: Implications for the Involvement of Nitric Oxide"*Proc. Natl. Adac. Sci.* 87:3629–3632 (1990).

Kilbourn et al., "Reversal of Endotoxin-Mediated Shock by $N^G$-Methyl-L-Arginine, an Inhibitor of Nitric Oxide Synthesis" *Biochem. Biophys. Res. Commun.* 172:1132–1138 (1990).

Kilbourn and Griffith, "Overproduction of Nitric Oxide in Cytokine-Mediated and Septic Shock" *J. Natl. Cancer Instit.* 84:827–831 (1992).

Kilbourn et al., "Cell-Free Hemoglobin Reverses the Endotoxin-Mediated Hyporesponsivity of Rat Aortic Rings to α-Adrenergic Agents" *Biochem. Biophys. Res. Commun.* 199:155–162 (1994).

Kilbourn et al., "$N^G$-Methyl-L-Arginine, an Inhibitor of Nitric Oxide Formation, Reverses IL-2-Mediated Hypotension in Dogs" *J. Appl. Physiol.* 76:1130–1137 (1994).

Kim et al., "Loss an Degradation of Enzyme-Bound Heme Induced by Cellular Nitric Oxide Sythesis" *J. Biol. Chem.* 270:5710–5713 (1995).

Komarov et al., "In Vivo Spin Trapping of Nitric Oxide in Mice" *Biochem. Biophys. Res. Commun.* 195:1191–1198 (1993).

Komarov and Lai, "Detection of Nitric Oxide Production in Mice by Spin-Trapping Electron Paramagnetic Resonance Spectroscopy" *Biochimica et Biophysica Acta* 1272:29–36 (1995).

Konturek et al., "Inhibition of Nitric Oxide Synthase Delays Healing of Chronic Gastric Ulcers" *Eur. J. Pharmacol.* 239:215–217 (1993).

Kovacs et al., "Increases in CD4 T Lymphocytes with Intermittent Courses of Interleukin-2 in Patients with Human Immunodeficiency Virus Infection" *New Eng. J. Med.* 332:567–575 (1995).

Lai and Komarov, "Spin Trapping of NItric Oxide Produced in vivo in Septic-Shock Mice" *FEBS Lett.* 345:120–124 (1994).

Lowenstein and Snyder, "Nitric Oxide, A Novel Biologic Messenger" *Cell* 70:705–707 (1992).

Lundberg et al., "Greatly Increased Luminal Nitric Oxide in Ulcerative Colitis" *Lancet* 344:1673–1674 (1994).

Luss et al., "Inhibition of Nitric Oxide Synthesis Enhances the Expression of Inducible Nitric Oxide Sythase mRNA and Protein in a Model of Chronic Liver Inflammation" *Biochem. Biophys. Res. Commun.* 204:635–640 (1994).

Middleton et al., "Increased Nitric Oxide Synthesis in Ulcerative Colitis" *Lancet* 341:465–466 (1993).

Miles et al., "Association Between Biosynthesis of Nitric Oxide and Changes in Immunological and Vascular Parameters in Patients Treated with Interleukin-2" *Eur. J. Clin. Invest.* 24:287–290 (1994).

Minnard et al., "Inhibition of Nitric Oxide Synthesis Is Detrimental During Endotoxemia" *Arch. Surg.* 129:142–148 (1994).

Mitaka et al., "Effects of Nitric Oxide Synthase Inhibitor on Hemodynamic Change and $O_2$ Delivery in Septic Dogs" *Am. J. Physiol.* 268:H2017–H2023 (1994).

Moncada, S., "The 1991 Ulf von Euler Lecture: The L-Arginine: Nitric Oxide Pathway" *Acta Physiol. Scand.* 145:201–227 (1992).

Moncada and Higgs, "The L-Arginine–Nitric Oxide Pathway" *New Eng. J. Med.* 329:2002–2012 (1993).

Ochoa et al., "Nitrogen Oxide Levels in Patients After Trauma and During Sepsis" *Ann. Surg.* 214:621–626 (1991).

Ogle and Qiu, "Nitric Oxide Inhibition Intensifies Cold-Restraint Induced Gastric Ulcers in Rats" *Experientia* 49:304–307 (1993).

Palmer, Richard M. J., "The discovery of Nitric Oxide in the Vessel Wall" *Arch. Surg.* 128:396–401 (1993).

Palmer et al., "Nitric Oxide Release Accounts for the Biological Activity of Endothelium-Derived Relaxing Factor" *Nature* 327:524–26 (1987).

Petros et al., "Effects of a Nitric Oxide Synthase Inhibitor in Humans with Septic Shock" *Cardiovascular Research* 28:34–39 (1994).

Petros et al., "Effect of Nitric Oxide Synthase Inhibitors on Hypotension in Patients with Septic Shock" *Lancet* 338:1557–1558 (1991).

Qazi et al., "Phase I Clinical and Pharmacokinetic Study of Diethyldithiocarbamate as a Chemoprotector From Toxic Effects of Cisplatin" *J. Natl. Cancer Inst.* 80:1486–1488 (1988).

Rachmilewitz et al., "Enhanced Gastric Nitric Oxide Synthase Activity in Duodenal Ulcer Patients" *Gut* 35:1394–1397 (1994).

Radomski & Moncada "Regulation of Vascular Homeostatsis by Nitric Oxide" *Thromb. Haemos.* 70:36–41 (1993).

Rees et al., "Role of Endothelium–Derived Nitric Oxide in the Regulation of Blood Pressure" *Proc. Natl. Acad. Sci. USA* 86:3375–3379 (1989).

Robertson et al., "Detrimental Hemodynamic Effects of Nitric Oxide Synthase Inhibition in Septic Shock" *Arch. Surg.* 129:149–156 (1994).

Rodeberg et al., "Nitric Oxide: An Overview" *Am. J. Surg.* 170:292–303 (1995).

Schilling et al., "A New Approach in the Treatment of Hypotension in Human Septic Shock by $N^G$–Monomethyl–L–Arginine, an Inhibitor of the Nitric Oxide Synthetase" *Intensive Care Medicine* 19:227–231 (1993).

Shinobu et al. "Sodium N–Methyl–D–Glucamine Dithiocarbamate and Cadmium Intoxication" *Acta Pharmacol. Toxicol.* 54:189–194 (1984).

St. John and Dorinsky, "Immunologic Therapy for ARDS, Septic Shock, and Multiple–Organ Failure" *Chest* 103:932–943 (1993).

Statman et al., "Nitric Oxide Inhibition in the Treatment of the Sepsis Syndrome is Detrimental to Tissue Oxygenation" *J. Surg. Res.* 57:93–98 (1994).

Stefanovic–Racic et al., "Nitric Oxide and Arthritis" *Arthrities and Rhumastism* 36:1036–1044 (1993).

Stefanovic–Racic et al., "N–Monomethyl Arginine, an Inhibitor of Nitric Oxide Synthase, Suppresses the Development of Adjuvant Arthritis in Rats" *Arhtritis & Rhumatism* 37:1062–1069 (1994).

Vallance and Moncada, "Hyperdynamic Circulation in Cirrhosis: a Role for Nitric Oxide?" *Lancet* 337:776–778 (1991).

Vallance and Moncada, "Nitric Oxide—From Mediator to Medicines" *Journal of the Royal College of Physicians of London* 28:209–219 (1994).

Waage & Steinshamn, "Cytokine Mediators of Septic Infections in the Normal and Granulocytopenic Host" *Eur. J. Haematol.* 50:243–249 (1993).

Winlaw et al., "Urinary Nitrate Excretion is a Noninvasive Indicator of Acute Cardiac Allograft Rejection and Nitric Oxide Production in the Rat" *Transplantation* 58:1031–1036 (1994).

Worrall et al., "Modulation of In Vivo Alloreactivity by Inhibition of Inducible Nitric Oxide Synthase" *J. Exp. Med.* 181:63–70 (1995).

Yang et al., "Induction of Myocardial Nitric Oxide Synthase by Cardiac Allograft Rejection" *J. Clin. Invest.* 94:714–721 (1994).

Zweier et al., "Direct Measurement of Nitric Oxide Generation in the Ischemic Heart Using Electron Paramagnetic Resonance Spectorscopy" *J. Bio. Chem.* 270:304–307 (1995).

Von Ritter et al., "Gastric Mucosal Lesions are Induced by Hemorrhagic Shock in Baboons. Role of Oxygen–derived Free Radicals". *Digestive Diseases and Sciences,* 33(7):857–864 (1988).

COMBINATIONAL THERAPEUTIC METHODS EMPLOYING NITRIC OXIDE SCAVENGERS AND COMPOSITIONS USEFUL THEREFOR

FIELD OF THE INVENTION

The present invention relates to methods for directly or indirectly treating the production of species which induce the expression of nitric oxide synthase in mammals. In a particular aspect, the present invention relates to methods for inactivating such species, or inhibiting the production of such species, while, at the same time, reducing nitric oxide levels, by co-administration of agents which inactivate (or inhibit the production of) such species, along with a dithiocarbamate compound as a scavenger of overproduced nitric oxide. In a further aspect, the present invention relates to compositions and formulations useful in the methods disclosed herein.

BACKGROUND OF THE INVENTION

In 1987, nitric oxide (.NO), a gaseous free-radical, was discovered in humans (see, for example, Ignarro et al., in *Proc. Natal. Acad. Sci., USA* 84:9265–69 (1987) and Palmer et al., in *Nature* 327:524–26 (1987)). As an indication of the significance of this discovery for the understanding of human physiology and pathophysiology, Science magazine selected nitric oxide as the molecule of the year in 1992.

Nitric oxide is formed from the terminal guanidino nitrogen atom of L-arginine by nitric oxide synthase (NOS; see, for example, Rodeberg et al., in *Am. J. Surg.* 170:292–303 (1995), and Bredt and Snyder in *Ann. Rev. Biochem.* 63:175–95 (1994)). Two major forms of nitric oxide synthase, constitutive and inducible enzymes, have been identified.

Under physiological conditions, a low output of .NO is produced by the constitutive, calcium-dependent NOS isoform (cNOS) present in numerous cells, including endothelium and neurons. This low level of nitric oxide is involved in a variety of regulatory processes, e.g., blood vessel homeostasis, neuronal communication and immune system function. On the other hand, under pathophysiological conditions, a high output of .NO is produced by the inducible, calcium-independent NOS isoform (iNOS) which is expressed in numerous cell types, including endothelial cells, smooth muscle cells and macrophages. These high levels of nitric oxide have been shown to be the etiology of endotoxin shock. This high output of .NO further contributes to inflammation-related tissue damage, neuronal pathology, N-nitrosamine-induced carcinogenesis and mutations in human cells and bacteria via deamination reaction with DNA. Nitric oxide can therefore be seen to be a mixed blessing, being very desirable when present in small amounts, while potentially being highly detrimental when produced in excessive quantities.

Nitric oxide is a potent vasodilator (see, for example, Palmer in *Arch. Surg.* 128:396–401 (1993) and Radomski & Moncada in *Thromb. Haemos.* 70:36–41 (1993). For example, in blood, .NO produced by the endothelium diffuses isotropically in all directions into adjacent tissues. As .NO diffuses into the vascular smooth muscle, it binds to guanylate cyclase enzyme, which catalyzes the production of cGMP, inducing vasodilation (see, for example, Ignarro, L. J., *Ann. Rev. Toxicol.* 30:535–560 (1990); Moncada, S., *Acta Physiol. Scand.* 145:201–227 (1992); and Lowenstein and Snyder, *Cell* 70:705–707 (1992)). The overproduction of nitric oxide causes an extreme drop in blood pressure, resulting in insufficient tissue perfusion and organ failure, syndromes that are associated with many diseases and/or conditions (e.g., septic shock, overexpression of cytokines, allograft rejection, and the like). The overproduction of nitric oxide is triggered by a number of stimuli, such as, the overproduction of inflammatory cytokines (e.g., tumor necrosis factor (TNF), interleukin-1 (IL-1), interferons, endotoxin, and the like). Additionally, the overproduction of .NO has been discovered to be one of the major side-effects of cytokine therapy (see, for example, Miles et al., in *Eur. J. Clin. Invest.* 24:287–290 (1994) and Hibbs et al., in *J. Clin. Invest.* 89:867–877 (1992)). Thus, abnormally elevated nitric oxide levels have been linked to many inflammatory and infectious diseases.

Inflammatory cytokines (e.g., TNF, interleukins or interferons) and infectious agents (e.g., endotoxin) induce nitric oxide overproduction by inducing transcription of the inducible nitric oxide synthase gene, leading to the production of inducible nitric oxide synthase, which in turn results in the overproduction of nitric oxide. The production of nitric oxide by the above-described pathway can be disrupted in a variety of ways. Thus, for example, there have been attempts to develop monoclonal antibodies (e.g., anti-endotoxin antibodies, anti-cytokine antibodies, anti-cytokine receptor antibodies, and the like) in efforts to block the .NO production pathway at the transcriptional level. Unfortunately, however, such efforts have met with very limited success (see, for example, Glauser et al., in *Clin. Infect. Dis.* 18:S205–16 (1994) and St. John & Dorinsky, in *Chest* 103: 932–943 (1993)). At least one reason for the relative lack of success in the art is the fact that the production of inflammatory cytokines is short-lived (see, for example, Wange & Steinsham in *Eur. J. Haematol.* 50:243–249 (1993)), while overproduction of nitric oxide lasts several days, causing systemic hypotension, insufficient tissue perfusion and organ failure.

Thus, for example, during endotoxemia, TNF production peaks at about 1–2 hours. Therefore, in order to be effective, anti-TNF antibodies would have to be administered at an early stage after infection. Indeed, in many clinical settings, patients are likely to already have been infected with bacteria prior to being admitted. Accordingly, such therapeutic methods have met with only limited success.

Currently, many pharmaceutical companies have turned their attention to the design and development of substrate or product analogue inhibitors of the enzyme, NOS, in efforts to treat the overproduction of .NO. However, recent data show that the inhibition of NOS is detrimental to subjects. For example, rodent studies show that inhibition of the production of nitric oxide causes intrauterine growth retardation and hind-limb disruptions in rats (see, for example, Diket et al., in *Am. J. Obstet. Gynecol.* 171:1243–1250 (1994)). Furthermore, the inhibition of nitric oxide synthesis during endotoxemia has also been shown to be detrimental (see, for example, Minnard et al., in *Arch. Surg.* 129:142–148 (1994); Luss et al., in *Biochem. Biophys. Res. Commun.* 204:635–640 (1994); and Hargrecht et al., in *J. Leuk. Biol.* 52:390–394 (1992)). Similar results have been reported in larger animal studies, such as dogs and swine (see, for example, Statman et al., in *J. Surg. Res.* 57:93–98 (1994); Mitaka et al., *Am. J. Physiol.* 268:H2017–H2023 (1994); Robertson, et al., *Arch. Surg.* 129:149–156 (1994); and Henderson et al., *Arch. Surg.* 129:1271–1275 (1994)).

Since a variety of stimuli induce expression of nitric oxide synthase, which, in turn, leads to nitric oxide overproduction (with its attendant detrimental effects), there is a need in the art to effectively treat both the initial stimulus of nitric oxide synthase expression, and the resulting overproduction of nitric oxide.

BRIEF DESCRIPTION OF THE INVENTION

In accordance with the present invention, combinational therapeutic methods have been developed for the in vivo inactivation or inhibition of formation (either directly or indirectly) of species which induce the expression of inducible nitric oxide synthase, as well as reducing nitric oxide levels produced as a result of .NO synthase expression. In contrast to the inhibitory approach described in the prior art to address the problem of nitric oxide overproduction (see, for example, Aisaka et al., *Biochem. Biophys. Res. Commun.* 60:881–886 (1989); Rees, et al., *Proc. Natl. Acad. Sci. USA* 86:3375–3379, (1989)); Henderson et al., in *Arch. Surg.* 129:1271–1275 (1994); Hambrecht et al., in *J. Leuk. Biol.* 52:390–394 (1992); Luss et al., in *Biochem. and Biophys. Res. Comm.* 204:635–640 (1994); Robertson et al., in *Arch. Surg.* 129:149–156 (1994); Statman et al., in *J. Surg. Res.* 57:93–98 (1994); and Minnard et al., in *Arch. Surg.* 129:142–148 (1994)), the present invention employs a combination of inactivation (and/or inhibition) and scavenging approach whereby the stimulus of nitric oxide synthase expression is inactivated and/or expression thereof is inhibited, and overproduced nitric oxide is bound in vivo to a suitable nitric oxide scavenger. The resulting complexes render the stimulus of nitric oxide synthase expression inactive (or inhibit the production thereof), while also rendering the resulting nitric oxide harmless. The resulting complexes are eventually excreted in the urine of the host. Further in accordance with the present invention, there have been developed compositions and formulations useful for carrying out the above-described methods.

Numerous stimuli for -NO synthase are known in the art. Co-administration of agents which inactivate the stimulus of .NO synthase expression (or inhibit the production thereof), in combination with nitric oxide scavengers as described herein, provides a more effective means to treat a variety of indications than has previously been described in the art.

An exemplary nitric oxide scavenger contemplated for use in the practice of the present invention is a dithiocarbamate-ferrous iron complex. This complex binds to .NO, forming a stable, water-soluble dithiocarbamate-iron-NO complex having a characteristic three-line spectrum (indicative of a mononitrosyl-Fe complex) which can readily be detected at ambient temperatures by electron paramagnetic resonance (EPR) spectroscopy (See Komarov et al., in *Biochem. Biophys. Res. Commun.* 195:1191–1198 (1993); and Lai and Komarov, *FEBS Lett.*,345:120–124, (1994)). This method of detecting .NO in body fluids in real time has recently been described by Lai in U.S. Pat. No. 5,358,703, incorporated by reference herein in its entirety.

The present invention relates to combinational therapeutic methods for treating the production of species which induce the expression of nitric oxide synthase in mammals. Thus, a dual attack is mounted against a variety of stimuli which lead to the production of dangerously high in vivo levels of .NO. Combinations of agents contemplated for use in the practice of the present invention (i.e., agents capable of inactivating species which induce expression of inducible nitric oxide, or agents which inhibit the production of such species, and dithiocarbamate-containing nitric oxide scavengers) are administered to a host in need of such treatment. The agent capable of inactivating (or inhibiting the production of) species which induce expression of inducible nitric oxide and .NO scavengers interact with the stimulus of nitric oxide synthase expression and in vivo produced .NO, respectively, forming a complex between said species and said agent, as well as a stable dithiocarbamate-metal-NO complex. Whereas free -NO is a potent vasodilator, .NO chelated with dithiocarbamate-iron complexes is not. The NO-containing complex is then filtered through the kidneys, concentrated in the urine, and eventually excreted by the subject, thereby reducing in vivo .NO levels.

DETAILED DESCRIPTION OF THE INVENTION

Figure 1:
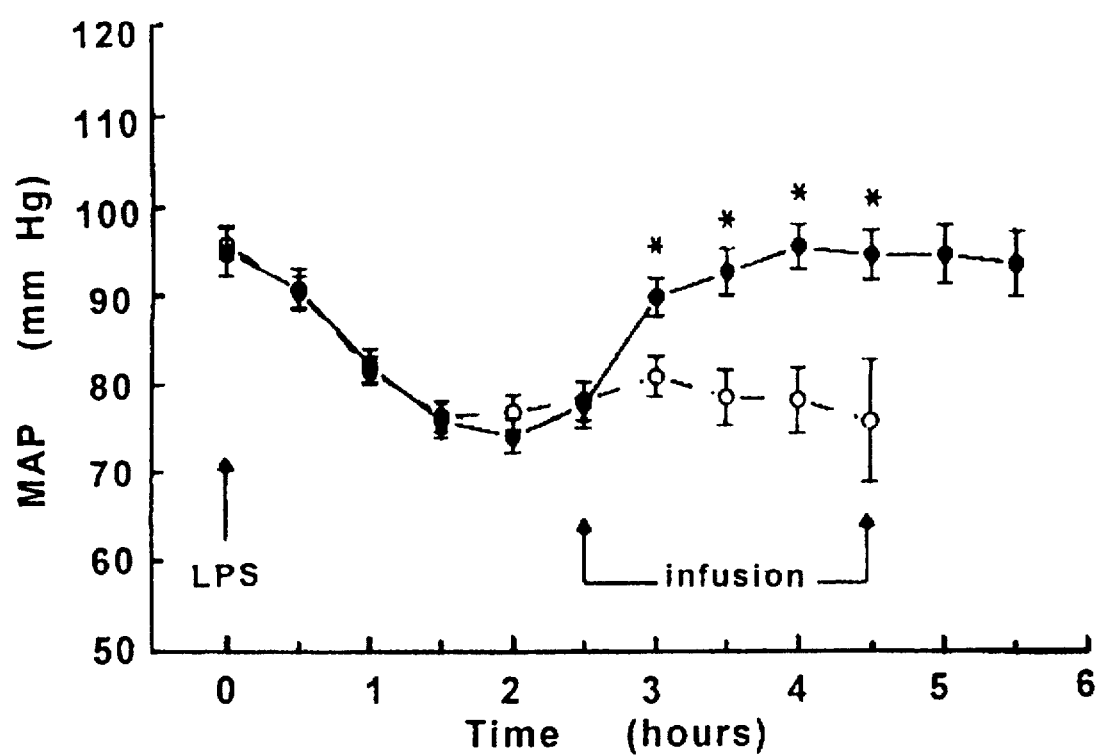
FIG. 1 illustrates the effects of endotoxin (LPS-4 mg/kg) treatment on mean arterial pressure (MAP) with and without [(MGD)$_2$/Fe] treatment. Bolus i.v. injection of LPS at time zero was as indicated in the Figure. Data marked by open circles [○] are the result of bolus i.v. injection of 1.0 ml saline, followed by 1.0 ml/hr of continuous saline infusion (n=$^{11}/_{16}$, note: 11 out of 16 animals died before the end of the experiments). Data marked by closed circles [●], are the result of [(MGD)$_2$/Fe] infusion, 0.1 mmole/kg loading dose followed by 0.1 mmole/kg/hr i.v. infusion (n=$^3/_{16}$, note: only 3 out of 16 animals died before the end of the experiments). Data points marked with an asterisk (*) indicate the results are significantly different at p <0.05. The ratio of MGD to Fe used was 5:1 (MGD:Fe), and the dosage shown was with respect to MGD.

In accordance with the present invention, there are provided combinational therapeutic methods for directly or indirectly treating the production of species which induce the expression of inducible nitric oxide synthase in a subject. Invention methods comprise:

co-administering to a subject an effective amount of a combination of at least one agent capable of directly or indirectly inactivating said species, or inhibiting production of said species, and at least one dithiocarbamate-containing nitric oxide scavenger.

Dithiocarbamate-containing nitric oxide scavengers contemplated for use in the practice of the present invention include any physiologically compatible derivative of the dithiocarbamate moiety (i.e., (R)$_2$N—C(S)—SH). Such compounds can be described with reference to the following generic structure (I)

$$[R_1R_2N-C(S)-S^-]_xM^{+1,+2,+3} \qquad (I)$$

wherein:

each R$_1$ and R$_2$ is independently selected from a C$_1$ up to C$_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl or R$_1$ and R$_2$ can cooperate to form a 5-, 6- or 7-membered ring including N, R$_1$ and R$_2$, x is 1 or 2, and M is a monovalent cation when x is 1, or M is a physiologically compatible divalent or trivalent transition metal cation when x is 2.

Presently preferred compounds having the above-described generic structure (I) are those wherein:

each of R$_1$ and R$_2$=a C$_1$ up to C$_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and $M=Fe^{+2}$ or $Fe^{+3}$.

Especially preferred compounds having the above-described generic structure are those wherein:

$R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and $M=Fe^{+2}$.

The presently most preferred compounds having the above-described generic structure are those wherein:

$R_1$=a $C_2$ up to $C_8$ alkyl or substituted alkyl, wherein the substituents are selected from carboxyl, acetyl, amido or hydroxy, $R_2$=a $C_1$ up to $C_4$ alkyl or substituted alkyl, and $M=Fe^{+2}$.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(0)— and/or —N(R)— containing alkylene moieties, wherein R is hydrogen or a lower alkyl moiety.

Monovalent cations contemplated for incorporation into compounds of structure (I) include $H^+$, $Na^+$, $NH_4^+$, tetraalkyl ammonium, and the like. Physiologically compatible divalent or trivalent transition metal cations contemplated for incorporation into the above compounds include charged forms of iron, cobalt, copper, manganese, or the like (e.g., $Fe^{+2}$, $Fe^{+3}$, $Co^{+2}$, $Co^{+3}$, $Cu^{+2}$, $Mn^{+2}$ or $Mn^{+3}$). In accordance with the present invention, the ratio of dithiocarbamate-species to counter-ion M can vary widely. Thus, dithiocarbamate-containing nitric oxide scavenger can be administered without any added metallic counter-ion (i.e., $M=H^+$, or a transition metal cation to dithiocarbamate-species ratio of zero), with ratios of transition metal cation to dithiocarbamate-species up to about 1:2 (i.e., a 2:1 dithiocarbamate:transition metal cation complex) being suitable.

As employed herein, "substituted alkyl" comprises alkyl groups further bearing one or more substituents selected from hydroxy, alkoxy (of a lower alkyl group; wherein a lower alkyl group has about 1–4 carbon atoms), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkylcarbonyl species.

As employed herein, "halogen" refers to fluoride, chloride, bromide or iodide atoms.

Induction of expression of inducible nitric oxide synthase, and hence, overproduction of nitric oxide, is associated with a wide range of disease states and/or indications, such as, for example, septic shock, ischemia, administration of cytokines, overexpression of cytokines, ulcers, inflammatory bowel disease (e.g., ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, and the like.

Treatment of such conditions can be carried out with such reagents as anti-cytokine antibodies, anti-cytokine receptor antibodies, anti-endotoxin antibodies, bradykinin antagonists, synthetic peptide blocking bradykinin receptors, bactericidal/permeability increasing protein, antibodies to platelet activating factor, and the like. Such agents can be used for a variety of indications, such as for example, anti-endotoxin therapy (e.g., antibodies to endotoxin, antibodies to LPS-binding protein, soluble CD14 protein, bactericidal/permeability increasing protein, polymyxin B, and the like), inhibition of cytokine synthesis/release (e.g., employing phosphodiesterase inhibitors, IL-4, IL-10, IL-13, TGF-β, corticosteroids, and the like), anti-cytokine therapy (e.g., employing antibodies to TNF, soluble TNF receptors, IL-1 receptor antagonists, antibodies to IL-1 receptors, antibodies to IL-6, antibodies to interferon-γ, soluble interferon-γ receptors, and the like), inhibition of the coagulation cascade (and of complement activation, employing such agents as anti-Factor XII antibodies antibodies to C5a, C1-esterase inhibitors, soluble Cr1, and the like), inhibition of platelet activating factor (PAF, employing such agents as PAF receptor antagonists), inhibition of arachidonate metabolism (e.g., employing agents such as cyclooxygenase inhibitors, lipoxygenase inhibitors, leukotriene inhibitors, thromboxane $A_2$ inhibitors, prostaglandins, and the like), inhibition of nitric oxide synthase enzymes (e.g., employing N-methyl-L-arginine, ε-N-iminoethyl-L-lysine, aminoguanidine, S-methyl isothiourea sulfate, and the like), immunosuppression (e.g., employing agents such as cyclosporin A, OKT3, FK506, and the like), diabetic therapy (e.g., employing agents such as free pancreatic islets, encapsulated pancreatic islets, oral insulin, intravenous insulin, amylin hormone, and the like), dihydropyridine calcium channel blockers (e.g., employing agents such as nifedipine, nitrendipine, nisoldipine, and the like), inflammatory disease therapy (e.g., employing agents such as sulfasalazine, mesalamine, corticosteroids, azathioprine, 6-mercaptopurine, metronidazole, aspirin, phenyl butyl nitrone (PBN), and the like), and so on.

Presently preferred indications for treatment in accordance with the present invention include septic shock, ischemia, ulcers, ulcerative colitis, diabetes, arthritis, asthma, Alzheimer's disease, Parkinson's disease, multiple sclerosis, cirrhosis or allograft rejection, and the like.

In accordance with a particular aspect of the present invention, the dithiocarbamate-containing nitric oxide scavenger is administered in combination with one or more of the above-described agents, optionally including an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmaceutical agents or the indication they are designed to address (e.g., systemic hypotension) can be prevented or reduced by co-administration of a combination reagent including a dithiocarbamate-containing nitric oxide scavenger.

Those of skill in the art recognize that the combination of an agent capable of inactivating species which induce the expression of inducible nitric oxide (or an agent capable of inhibiting the production of such species), and dithiocarbamate-containing nitric oxide scavengers described herein can be delivered in a variety of ways, such as, for example, orally, intravenously, subcutaneously, parenterally, rectally, by inhalation, and the like.

Since individual subjects may present a wide variation in severity of symptoms and each drug has its unique therapeutic characteristics, the precise mode of administration, dosage employed and treatment protocol for each subject is left to the discretion of the practitioner.

In accordance with still another embodiment of the present invention, there are provided physiologically active composition(s) comprising an "agent" and a compound having the structure I, as described above, in a suitable vehicle rendering said compound amenable to oral delivery, transdermal delivery, intravenous delivery, intramuscular delivery, topical delivery, nasal delivery, and the like.

Depending on the mode of delivery employed, the above-described compositions can be delivered in a variety of pharmaceutically acceptable forms. For example, the above-described compositions can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more each of the scavenging and inhibiting compounds contemplated for use in the practice of the present invention, as active ingredients thereof, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds (i.e., "agents" and compounds of structure I as described herein) are included in the pharmaceutical composition in an amount sufficient to produce the desired effect upon the target process, condition or disease.

Pharmaceutical compositions containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions. In addition, such compositions may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

Since individual subjects may present a wide variation in severity of symptoms and each active ingredient has its unique therapeutic characteristics, it is up to the practitioner to determine a subject's response to treatment and vary the dosages accordingly.

Typical daily doses of dithiocarbamate-containing nitric oxide scavengers, in general, lie within the range of from about 10 µg up to about 100 mg per kg body weight, and, preferably within the range of from 50 µg to 10 mg per kg body weight and can be administered up to four times daily. The daily IV dose lies within the range of from about 1 µg to about 100 mg per kg body weight, and, preferably, within the range of from 10 µg to 10 mg per kg body weight.

In general, the dosage of dithiocarbamate-containing nitric oxide scavenger employed in the practice of the present invention falls in the range of about 0.01 mmoles/kg body weight of the subject/hour up to about 0.5 mmoles/kg/hr.

The invention will now be described in greater detail by reference to the following non-limiting examples.

EXAMPLE 1

Wistar rats (male, 230–300 g) were supplied by Simonson Laboratories (Gilroy, Calif.).

Lipopolysaccharide (LPS; S. typhosa, endotoxin) was obtained from Sigma (St. Louis, Mo.).

N-Methyl-D-glucamine and carbon disulfide were obtained from Aldrich (Milwaukee, Wis.). N-Methyl-D-glucamine dithiocarbamate (MGD) was synthesized by following the method of Shinobu et al. (*Acta Pharmacol. Toxicol.* 54:189–194 (1984)).

EXAMPLE 2

As described previously (see Lai and Komarov in *FEBS Lett.* 345:120–124 (1994)), one [(MGD)$_2$/Fe] complex binds to one molecule of nitric oxide to form a [(MGD)$_2$/Fe—NO] complex. Whereas free nitric oxide is a potent vasodilator, nitric oxide bound to [(MGD)$_2$/Fe] is not. The resulting complex is then excreted from the body in the urine, thereby reducing in vivo nitric oxide levels.

The effects of [(MGD)$_2$/Fe] treatment on the mean arterial pressure of endotoxemia in rats are shown in FIG. 1. When rats were treated with lethal doses of LPS, the mean arterial pressure dropped gradually with time and reached 75 mm Hg at the end of 2 hours. In controls, when the animals were infused with saline, their mean arterial pressure remained very low; indeed, 11 out of 16 animals died before the end of the experiments. On the other hand, when the LPS-treated animals were infused with [(MGD)$_2$/Fe], their mean arterial pressure gradually restored to normal levels, and only 3 out of 16 animals died before the end of the experiments. Therefore, infusions of [(MGD)$_2$/Fe] can not only restore blood pressure, but also reduces the mortality rate in endotoxin induced septic shock rats.

In summary, [(MGD)$_2$/Fe] is potentially useful for the treatment of systemic hypotension (extreme drop in blood pressure), caused by abnormally elevated levels of nitric oxide; a condition which has been associated with many inflammatory and infectious diseases. In addition, [(MGD)$_2$/Fe] has been shown to be safe inasmuch as the animals survived after injections of up to 1% of their body weight without apparent side effects (Lai and Komarov, supra).

EXAMPLE 3

As previously described (see Komarov and Lai in *Biochim. Biophys. Acta* 1272:29–36 (1995)), subcutaneous administration of the [(MGD)$_2$/Fe] complex reduced in vivo .NO levels in LPS-treated mice. Since excessive .NO production is known to induce systemic hypotension, injections of the [(MGD)$_2$/Fe] complex that reduce in vivo .NO levels should also restore blood pressure in hypotensive animals induced by LPS treatment. To test this idea, experiments were carried out to determine the effects of administration of the [(MGD)$_2$/Fe] complex on the blood pressure of the hypotensive rats induced by LPS challenge.

Thus, male Wistar rats (230–300 g) fasted overnight were anesthetized with thiobutabarbital (Inactin, 100 mg/kg, i.p.). A catheter was implanted in the femoral vein for drug infusions. The femoral artery was cannulated for continuous blood pressure measurement. Rats were injected with an i.v. bolus dose of LPS (S.Typhosa endotoxin, 4 mg/kg). Two hours after LPS challenge, rats were then subjected to one of the following treatments:

(a) Control, saline infusion—1.0 ml saline i.v. injection followed by 1.0 ml/hr of saline infusion for 2.0 hours, (b) [(MGD)$_2$/Fe] (at a ratio of 2-to-0.4)—0.1 mmole/kg i.v. bolus injection followed by 0.1 mmole/kg infusion for 2.0 hours, (c) [(MGD)$_2$/Fe] (at a ratio of 2-to-0.2)—0.1 mmole/kg i.v. bolus injection followed by 0.1 mmole/kg infusion for 2.0 hours, and (d) [(MGD)$_2$/Fe] (at a ratio of 2-to-0)—0.1 mmole/kg i.v. bolus injection followed by 0.1 mmole/kg infusion for 2.0 hours.

The results of mean arterial pressure (MAP) measurement as a result of each of these treatments are summarized in Table 1.

TABLE 1

Effects of various ratios of [(MGD)$_2$/Fe] treatment on the mean arterial pressure (MAP in mmHg) in lipopolysaccharide (LPS)-induced shock rats

| Conditions[1] | Baseline[2] (mean ± SEM) | 2 hrs after LPS Exposure | 2.0 hrs after Treatment |
|---|---|---|---|
| a) Control saline (n = 16)[3] | 96 ± 2 | 77 ± 2 | 76 ± 7 |
| b) [(MGD)$_2$/Fe] (2/0.4)[4] (n = 16) | 95 ± 3 | 75 ± 2 | 95 ± 3 |
| c) [(MGD)$_2$/Fe] (2/0.2) (n = 9) | 98 ± 2 | 75 ± 3 | 89 ± 4 |
| d) MGD (2/0) (n = 9) | 99 ± 4 | 71 ± 2 | 94 ± 6 |

[1]Experimental conditions were as described in the text.
[2]The values of MAP prior to LPS treatment.
[3]n, the number of animals in each group.
[4][(MGD)$_2$/Fe] (2/0.4) is defined as the ratio of [(MGD)$_2$/Fe] to be 2-to-0.4.

The MAP of anesthetized rats was in the range of 96 to 99 mmHg. Two hours after LPS treatment, the MAP decreased to between 71 and 77 mmHg, which is indicative of the onset of systemic hypotension, caused by abnormally elevated levels of nitric oxide, as also shown in FIG. 1. While the 2.0 hr saline infusion did not change the MAP, infusions of [(MGD)$_2$/Fe] complex at various ratios, ranging from 2-to-0.4 (MGD to Fe) to 2-to-0 (MGD to Fe), restored the blood pressure to 89–95 mmHg (Table 1). These results 10 suggest that the i.v. infusion of MGD either with or without added iron (Fe), can restore blood pressure in hypotensive rats induced by LPS challenge (Table 1).

Since MGD does not bind .NO, it is speculated that the restoration of the MAP by MGD infusion may be attributed to the MGD chelation of cellular iron released by excess .NO production, which is known to attack cellular iron-containing proteins and result in cellular iron loss during sepsis or septic shock (see, for example, Kim et al., in *J. Biol. Chem.* 270:5710–5713 (1995)).

This example shows that dithiocarbamate-containing nitric oxide scavengers, such as MGD, either with or without added iron, are effective for the treatment of systemic hypotension, a condition which is associated with many inflammatory and/or infectious diseases.

EXAMPLE 4

In order to test the efficacy of the combinational therapy of [(MGD)$_2$/Fe] and anti-TNF antibody for treatment of LPS-induced shock, Wistar rats are anesthetized with Ketamine/Xylazine (55 mg/kg plus 5.5 mg/kg). A catheter is implanted in the femoral vein for drug administration. The femoral artery is cannulated for continuous blood pressure measurement. The animals are allowed to recover from surgery for a period of 3 days prior to experimentation. On the day of the experiment, the conscious rats are retained in restrainers and the artery line is connected to the pressure transducer for recording. Rats are injected with an i.v. bolus dose of LPS (S. Typhosa, endotoxin, 10–20 mg/kg). Two hours after LPS challenge, rats are then subjected to one of the following treatments (8 animals in each group):

(1) Control, saline infusion—1.0 ml saline/hr of saline infusion for 6 hours.

(2) [(MGD)$_2$/Fe] (at a ratio of 5 to 1)—0.1 mmole/kg/hr infusion for 3 hours, followed by saline infusion for 3 hours.

(3) Anti-TNF—7.5 mg/kg/hr infusion for 3 hours, followed by saline infusion for 3 hours.

(4) Co-infusion of [(MGD)$_2$/Fe] (0.1 mmole/kg/hr) and Anti-TNF (7.5 mg/kg/hr) for 3 hours, followed by saline infusion for 3 hours.

(5) [(MGD)$_2$/Fe] (at a ratio of 5-to-1)—0.1 mmole/kg/hr infusion for 3 hours and followed by anti-TNF (7.5 mg/kg/hr) infusion for 3 hours.

At the end of the infusion, rats are returned to their cages for observation. The 24-hr survival rates resulting from these various treatments are compared. Since a lethal dose of LPS is used, it is expected that all animals in control group 1 will die within 24 hours. Based on the results presented in FIG. 1 (Example 2), it is expected that about two thirds of the rats in the treatment group (i.e., group 2, treated with [(MGD)$_2$/Fe]) will survive after 24 hours. As discussed above, in endotoxemia, TNF production is short-lived and peaks at 1–2 hours. Therefore, the infusion of anti-TNF antibodies at two hours after LPS challenge as indicated in group 3 may not be able to block the induction of the inducible nitric oxide synthase gene, which results in the production of iNOS, resulting in the overproduction of nitric oxide. In group 4, the co-infusion of anti-TNF antibodies and [(MGD)$_2$/Fe] is expected to produce a similar survival rate as that for group 2, employing [(MGD)$_2$/Fe] infusion alone. On the other hand, it is expected that the infusion of [(MGD)$_2$/Fe] for 3 hours, followed by the infusion of anti-TNF antibodies (as done with group 5) will improve the survival rate over that in group 2, because the infusion of anti-TNF antibodies at later hours would inhibit further activation of the inducible NO synthase gene, thereby reducing the further enhancement of excessive NO production.

The efficacies of combinational therapy between [(MGD)$_2$/Fe] and other therapeutic agents (such as anti-endotoxin antibodies, other anti-cytokine antibodies, anti-cytokine receptor antibodies, and other agents, such as antibradykinin peptides, nitric oxide synthase inhibitors, and the like) can be demonstrated in a similar fashion to that described herein.

While the invention has been described in detail with reference to certain preferred embodiments thereof, it will be understood that modifications and variations are within the spirit and scope of that which is described and claimed.

That which is claimed is:

1. A method for directly or indirectly treating the production of species which induce the expression of inducible nitric oxide synthase in a subject, said method comprising:
co-administering to said subject an effective amount of a combination of at least one agent capable of directly or indirectly inactivating said species, or inhibiting production of said species, and at least one dithiocarbamate-containing nitric oxide scavenger.

2. A method according to claim 1 wherein said species is selected from cytokines, cytokine receptors, endotoxins, platelet activating factor, bradykinin, bradykinin receptor, peptidoglycan, lipoteichoic acid, coagulation factors, arachidonate metabolites or nitric oxide synthase.

3. A method according to claim 1 wherein said agent is selected from anti-endotoxin agents, inhibitors of cytokine synthesis/release, anti-cytokine agents, inhibitors of the coagulation cascade, inhibitors of complement activation, inhibitors of platelet activating factor, inhibitors of arachidonate metabolism, inhibitors of nitric oxide synthase enzymes, immunosuppressive agents, diabetic therapeutic agents, therapeutic agents for inflammatory diseases or therapeutic agents for Crohn's disease therapy.

4. A method according to claim 1 wherein said agent is selected from anti-endotoxin agents, anti-cytokine agents, inhibitors of nitric oxide synthase enzymes, immunosuppressive agents or therapeutic agents for inflammatory diseases.

5. A method according to claim 1 wherein said dithiocarbamate-containing nitric oxide scavenger comprises a dithiocarbamate moiety having the structure (I), optionally associated with a physiologically compatible di- or tri-valent transition metal ion, wherein structure (I) is as follows:

$$[R_1R_2N-C(S)-S^-]_xM^{+1,+2,+3} \quad (I)$$

wherein:

each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, or $R_1$ and $R_2$ can cooperate to form a 5-, 6- or 7-membered ring including N, $R_1$ and $R_2$, x is 1 or 2, and M is a monovalent cation when x is 1, or M is a physiologically compatible divalent or trivalent transition metal cation when x is 2.

6. A method according to claim 5 wherein the ratio of transition metal ion to dithiocarbamate moiety falls in the range of zero up to about 1:2.

7. A method according to claim 5 wherein said physiologically compatible di- or tri-valent transition metal is selected from iron, cobalt, copper or manganese.

8. A method according to claim 1 wherein said combination of at least one agent, and at least one dithiocarbamate-containing nitric oxide scavenger is delivered orally, intravenously, subcutaneously, parenterally, rectally or by inhalation.

9. A method according to claim 1 wherein said combination of at least one agent, and at least one dithiocarbamate-containing nitric oxide scavenger is delivered in the form of a solid, solution, emulsion, dispersion, micelle or liposome.

10. In a therapeutic process which employs an agent to inactivate materials which, directly or indirectly, induce the expression of inducible nitric oxide synthase, the improvement comprising co-administering to a patient in need thereof a dithiocarbamate-containing nitric oxide scavenger in combination with said agent.

11. A method according to claim 10 wherein said agent is selected from anti-endotoxin agents, inhibitors of cytokine synthesis/release, anti-cytokine agents, inhibitors of the coagulation cascade, inhibitors of complement activation, inhibitors of platelet activating factor, inhibitors of arachidonate metabolism, inhibitors of nitric oxide synthase enzymes, immunosuppressive agents, diabetic therapeutic agents, therapeutic agents for inflammatory diseases or therapeutic agents for Crohn's disease therapy.

12. A composition comprising a combination of an agent capable of inactivating materials which, directly or indirectly, induce the expression of inducible nitric oxide synthase and a compound having structure (I) in a pharmaceutically acceptable carrier therefor, wherein said compound having structure (I) is as follows:

$$[R_1R_2N-C(S)-S^-]_xM^{+1,+2,+3} \quad (I)$$

wherein:

each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl or $R_1$ and $R_2$ can cooperate to form a 5-, 6- or 7-membered ring including N, $R_1$ and $R_2$, x is 1 or 2, and M is a monovalent cation when x is 1, or M is a physiologically compatible divalent or trivalent transition metal cation when x is 2.

13. A composition according to claim 12 wherein M is selected from $H^+$, $Na^+$, $NH_4^+$ or tetraalkyl ammonium.

14. A composition according to claim 12 wherein M is selected from $Fe^{+2}$, $Fe^{+3}$, $Co^{+2}$, $Co^{+3}$, $Cu^{+2}$, $Mn^{+2}$ or $Mn^{+3}$.

15. A composition according to claim 12 wherein the ratio of transition metal ion to dithiocarbamate moiety falls in the range of zero up to about 1:2.

16. A composition according to claim 12 wherein:

each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and M=$Fe^{+2}$ or $Fe^{+3}$.

17. A composition according to claim 12 wherein:

$R_1$=a $C_2$ up to $C_8$ alkyl or substituted alkyl, wherein said substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and M=$Fe^{+2}$.

18. A composition according to claim 12 wherein:

$R_1$=a $C_2$ up to $C_8$ alkyl or substituted alkyl, wherein said substituents are selected from carboxyl, acetyl, amido or hydroxy, $R_2$=a $C_1$ up to $C_4$ alkyl or substituted alkyl, and M=$Fe^{+2}$.

19. A composition according to claim 12 wherein said agent is selected from anti-endotoxin agents, inhibitors of cytokine synthesis/release, anti-cytokine agents, inhibitors of the coagulation cascade, inhibitors of complement activation, inhibitors of platelet activating factor, inhibitors of arachidonate metabolism, inhibitors of nitric oxide synthase enzymes, immunosuppressive agents, diabetic therapeutic agents, therapeutic agents for inflammatory diseases or therapeutic agents for Crohn's disease therapy, anti-cytokine antibodies, anti-cytokine receptor antibodies, anti-endotoxin antibodies, bradykinin antagonists, synthetic peptide blocking bradykinin receptors, bactericidal/permeability increasing protein or antibodies to platelet activating factor.

20. A composition according to claim 19 wherein said anti-endotoxin agent is selected from antibodies to endotoxin, antibodies to LPS-binding protein, soluble CD14 protein, bactericidal/permeability increasing protein or polymyxin B.

21. A composition according to claim 19 wherein said inhibitor of cytokine synthesis/release is selected from phosphodiesterase inhibitors, IL-4, IL-10, IL-13, TGF-β, aspirin, phenyl butyl nitrone or corticosteroids.

22. A composition according to claim 19 wherein said anti-cytokine agent is selected from antibodies to TNF, soluble TNF receptors, IL-1 receptor antagonists, antibodies to IL-1 receptors, antibodies to IL-6, antibodies to interferon-γ or soluble interferon-γ receptors.

23. A composition according to claim 19 wherein said inhibitor of the coagulation cascade is selected from anti-Factor XII antibodies, antibodies to C5a, C1-esterase inhibitors or soluble Cr1.

24. A composition according to claim 19 wherein said inhibitor of platelet activating factor is a PAF receptor antagonist.

25. A composition according to claim 19 wherein said inhibitor of arachidonate metabolism is selected from cyclooxygenase inhibitors, lipoxygenase inhibitors, leukotriene inhibitors, thromboxane $A_2$ inhibitors, or prostaglandins.

26. A composition according to claim 19 wherein said inhibitor of nitric oxide synthase enzymes is selected from N-methyl-L-arginine, ε-N-iminoethyl-L-lysine, aminoguanidine or S-methyl isothiourea sulfate.

27. A composition according to claim 19 wherein said immunosuppressive agent is selected from cyclosporin A, OKT3 or FK506.

28. A composition according to claim 19 wherein said diabetic therapeutic agent is selected from free pancreatic islets, encapsulated pancreatic islets, oral insulin, intravenous insulin, or amylin hormone.

29. A composition according to claim 19 wherein said therapeutic agent for inflammatory disease is selected from sulfasalazine, mesalamine, corticosteroids, azathioprine, 6-mercaptopurine, or metronidazole.

30. A composition according to claim 19 wherein said therapeutic agent for inflammatory disease is a dihydropyridine calcium channel blocker.

31. A composition according to claim 19 wherein said agent is selected from anti-endotoxin agents, inhibitors of cytokine synthesis/release, anti-cytokine agents, inhibitors of the coagulation cascade, inhibitors of complement activation, inhibitors of platelet activating factor, inhibitors of arachidonate metabolism, inhibitors of nitric oxide synthase enzymes, immunosuppressive agents, diabetic therapeutic agents, therapeutic agents for inflammatory diseases or therapeutic agents for Crohn's disease therapy, anti-cytokine antibodies, anti-cytokine receptor antibodies, anti-endotoxin antibodies, bradykinin antagonists, synthetic peptide blocking bradykinin receptors, bactericidal/permeability increasing protein or antibodies to platelet activating factor.

32. A composition according to claim 12 wherein said pharmaceutically acceptable carrier is selected from a solid, solution, emulsion, dispersion, micelle or liposome.

33. A composition according to claim 12 wherein said composition further comprises an enteric coating.

* * * * *